United States Patent [19]

Hedges

[11] 3,967,626

[45] July 6, 1976

[54] CALF EXTRACTOR

[76] Inventor: Wendell L. Hedges, P.O. Box 67, Seiling, Okla. 73663

[22] Filed: Mar. 12, 1975

[21] Appl. No.: 557,851

[52] U.S. Cl. .......... 128/352
[51] Int. Cl.² .......... A61D 1/08; A61B 17/42
[58] Field of Search .......... 128/352, 353

[56] References Cited

UNITED STATES PATENTS

| | | | |
|---|---|---|---|
| 2,522,508 | 9/1950 | Frank | 128/352 |
| 3,183,911 | 5/1965 | Anglemyer | 128/353 |
| 3,863,642 | 2/1975 | Weiland | 128/353 X |
| 3,870,049 | 3/1975 | Weiland | 128/353 |

*Primary Examiner*—Channing L. Pace
*Attorney, Agent, or Firm*—Robert K. Rhea

[57] ABSTRACT

An elongated shaft is adapted to be connected at one end with a breeching bar transversely engaging the rump of a cow and having a windlass connected with its other end. Friction grip means transversely surrounds the shaft intermediate its ends and projects laterally therefrom. A remote end of the grip means is connected with one end of a flexible obstetrical member adapted to be connected at its other end with an unborn calf. A windlass is connected with the grip means adjacent the shaft so that when tension is applied to the line and obstetrical member the grip means is slidable relative to the shaft and frictionally grips the shaft in a binding action upon release of tension on the line or obstetrical member.

1 Claim, 3 Drawing Figures

CALF EXTRACTOR

BACKGROUND OF THE INVENTION:

1. Field of the invention.

The present invention relates to animal husbandry and more particularly to means for extracting an unborn calf from the mother cow or assisting parturition.

When the natural means of birth fails for any one several reasons it is usually necessary to assist the mother cow in parturition to save the life of both the calf and cow. Young cows generally have difficulty in calving the first time and it is usually impractical, economically, with stock cattle, to await the services of a veterinarian. The function of assisting a mother cow can usually be performed by the rancher having one of the devices comprising this invention.

2. Description of the prior art.

Prior patents disclosing apparatus for assisting parturition of animals, such as cows, have generally comprised a breeching bar engaging the haunches of the mother animal which is provided with an elongated shaft supporting a hand operated winch usually provided with ratchet means which produces a generally unsatisfactory jerky and uneven pulling action on the animal resulting in injury to the calf or its mother. Further, a ratchet type winch involves more tooling in construction, than a simple windlass, for example, and when the line is fully wound on a ratchet type winch it is not easily released in a free wheeling action for extending its line for attachment to the unborn animal when setting up the device to assist the birth.

This invention overcomes the above disadvantages by providing a reel axially connected with a shaft and provided with a handle for operation in a windlass fashion to provide a steady and slow pull on the unborn animal. The device further includes means for maintaining tension on an obstetrical member on which tension is automatically maintained by friction grip means surrounding and gripping the shaft when the windlass action is stopped with the friction grip means being released by tension reapplied to the windlass line to continue the pulling operation.

SUMMARY OF THE INVENTION

A generally U-shaped breeching bar having its bight portion formed by a bar which transversely engages the rump of a cow with the legs of the U-shaped extending forwardly and around the haunches of the cow with the ends of the legs supported by a flexible member entrained transversely over the cow's hips. The breeching bar is further provided with an elongated tubular member forming an elongated socket projecting rearwardly of the cow.

An elongated shaft is adapted at one end portion to be telescopically received by the end of the socket opposite the cow and journals a reel at its other end. An elongated handle is transversely connected with one flange of the reel for rotating the latter and winding and unwinding a line in windlass fashion. A friction grip member transversely and loosely surrounds the shaft intermediate its ends and projects laterally of the shaft at one end portion. The laterally projecting end of the grip means is connected with one end of a flexible obstetrical member adapted to be connected at its other end with an unborn calf. The end of the windlass line opposite the reel is connected with the grip means between the shaft and its laterally projecting end so that when tension is applied to the grip means by the windlass line the grip means in turn places tension on the obstetrical member so that the grip means slides longitudinally along the shaft. When the tension on the windlass is released the laterally projecting end of the grip means tilts toward the axis of the shaft and frictionally grips opposite surfaces of the shaft to maintain tension on the obstetrical member. When tension is reapplied to the windlass line the grip means releases its grip on the shaft and applies such tension to the obstetrical member.

The principal object of this invention is to provide a calf extracting apparatus which is relatively economical when compared with this type of device presently in use and which is easily and quickly assembled from a knock-down storage position to an operating position for providing a steady pull on or applying pressure in a novel manner to the mother being assisted.

DESCRIPTION OF THE PREFERRED EMBODIMENT

Figures 1, 2, 3:
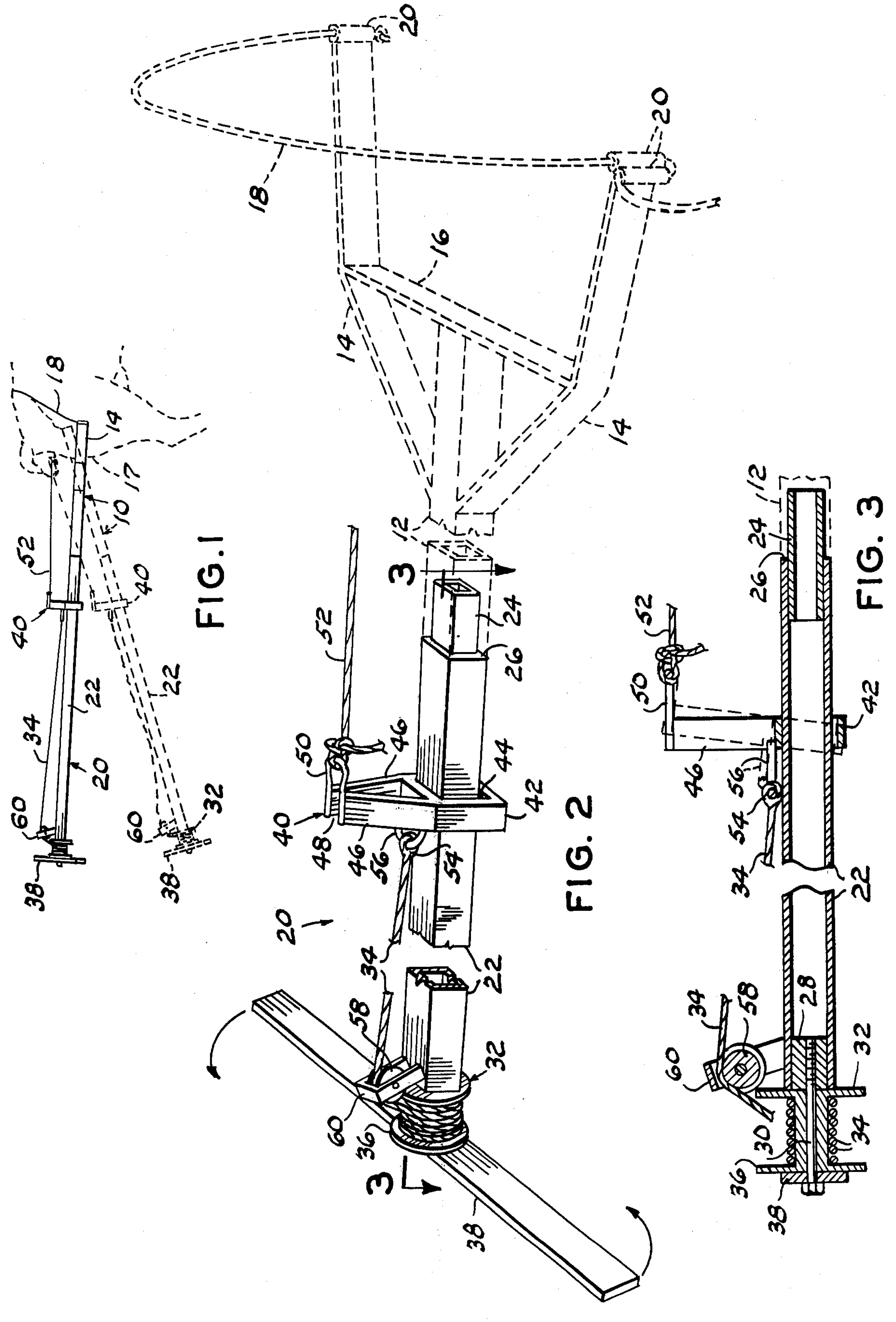
FIG. 1 is a side elevational view of the device in operative position to assist a cow in calving, a fragment of the cow being illustrated by dotted lines, and, also illustrating, by dotted lines, vertical movement of the device.
FIG. 2 is a fragmentary perspective view of the device when connected with a conventional breeching bar, the latter being shown by dotted lines; and, FIG. 3 is a vertical cross sectional view taken substantially along the line 3—3 of FIG. 2.

Like characters of reference designate like parts in those figures of the drawings in which they occur.

In the drawings:

The reference numeral 10 indicates a breeching bar, as a whole, comprising an elongated tubular member 12 forming a socket and having diverging leg members 14 connected across the adjacent end of the tube 12 by a cross bar 16 so that the cross bar and end portions of the legs 14, extending beyond cross bar 16, substantially describe a U-shape to straddle and engage the haunches 17 of a cow attempting to give birth. The free ends of the legs are supported by a rope 18, or the like, adjustably connected to the respective ends of the legs by sleeves 20 connected with the legs and the rope entrained over the hip portions of the cow forwardly of her tail base. The above described breeching bar 10 is substantially conventional and is set forth to illustrate the manner in which the invention is used therewith.

The reference numeral 20 indicates the improved tension producing windlass portion comprising an elongated shaft 22 having a reduced end portion 24 defined by an abrupt shoulder 26 to form a stop when the end portion 24 is telescoped into the end of the member 12 opposite the legs 14. The other end portion of the tube 22 is axially provided with a filler block 28 having a central bore which receives a bolt, or the like, forming an axle 30 for journalling a windlass forming reel 32 with the reel being rotatable about the axis of the shaft 22 and having a windlass line 34 secured at one end thereto and windable thereon. The flange 36, of the reel opposite the shaft 22, is connected with an elongated handle 38 intermediate its end for winding the windlass line 34 on the reel as presently explained.

A friction gripping member 40, comprising a sleeve-like frame 42, transversely surrounds the shaft 22 intermediate its ends and is slidable longitudinally of the shaft. The thickness or length of the frame, longitudinally of the shaft, is relatively narrow when compared with the transverse dimension of the shaft. The opening 44, defined by the sleeve frame loosely surrounds the shaft 22 so that when the sleeve is tilted toward or away from the breeching bar 10 the sleeve frictionally grips opposing surfaces of the shaft 22 for the purpose presently explained.

The gripping member 40 is further characterized by a pair of arms 46 secured to the sleeve frame 42 and projecting upwardly in converging relation, as viewed in the drawings, terminating in spaced relation to form a slot 48. The upper end portions of the arms 46 are connected with the respective leg portions of a U-shaped loop 50 with the bight portion of the loop disposed toward the breeching bar 10.

A flexible obstetrical, member 52 is adjustably connected at one end portion as by tying it to the U-shaped loop 50. The other end portion of the member 52 is adapted to be connected in a conventional manner with a portion of the unborn animal. The purpose of the slot 48, between the frame legs 46, is for ease in adjusting the length of the member 52 or for receiving and holding a chain, or the like, not shown, used as an obstetrical member or for a fragmentary portion of a chain connected to the strand-like obstetrical member 52.

The other end portion 54 of the windlass line 34 is secured to a rod-like eye 56 secured to the friction gripping member 40 opposite the breeching bar 10. The windlass line 34 is entrained over a small pulley 58 mounted between the legs of an inverted U-shaped bracket 60 secured to the surface of the shaft 22 adjacent the reel 32 and projecting laterally of the shaft in the direction of the frame arms 46. As shown in FIG. 2, the bracket 60 is tilted or inclined toward the reel 32 and rotated about its longitudinal axis to dispose the plane of the pulley at an acute angle with respect to the cylindrical plane generated by rotation of the reel. The axis of the pulley 58 is thus angularly disposed with respect to the axis of the shaft 22 to guide the windlass line 34 toward the reel when winding the line thereon.

The tube 12 and shaft 22 are shown substantially square in transverse cross section to prevent relative angular rotation but obviously may be of any other cross section configuration desired.

OPERATION

In operation, the breeching bar 10 is disposed on a cow as shown by FIG. 1, and described hereinabove. The tension generating or windlass portion 20 is axially joined to the breeching bar socket 12 and the obstetrical line secured to the animal whose birth is to be assisted and to the gripping member loop 50 with the gripping member 40 being disposed toward the end of the shaft adjacent the breeching bar. The gripping member 40 is initially easily moved manually along the shaft by simply pulling on the windlass line 34 which rotates the reel handle about the axle 30 and unwinds the line off the reel. Thereafter, the operator manually supports the device by the handle and rotates the handle in the direction of the arrows to apply tension to the obstetrical member 52 and in turn on the unborn animal. Such action tends to elevate the reel end portion of the shaft with respect to the surface of the earth, as shown by solid lines (FIG. 1). With tension on the obstetrical line 52 the reel end portion of the shaft is then lowered toward or to the dotted line position of FIG. 1 thus providing a fulcrum point where the breech cross bar 16 contacts the cow's haunches 17 so that a steady pull of greater magnitude than that applied by the windlass line 34 is applied to the unborn animal tending to cause the cow to elevate or hump her back which is a desirable action for a cow attempting to give birth. This action does not require that the operator maintain a tension on the windlass line for the reason the gripping member 40 frictionally grips the shaft 22 in a binding action thereon to prevent relative movement between the gripping member and shaft. After lowering the reel end of the shaft, to the dotted line position of FIG. 1, the shaft 22 may be again horizontally disposed and the windlass operated by the handle wherein tension applied to the gripping member 40 continues its movement toward the reel end of the shaft. The above action sequence is repeated as necessary.

Obviously the invention is susceptible to changes or alterations without defeating its practicability. Therefore, I do not wish to be confined to the preferred embodiment shown in the drawings and described herein.

I claim:

1. In combination with a parturifacient breeching bar of general U-shape having a bar portion adapted to transversely engage the rump of a cow and having legs adapted to extend forwardly along the haunches of a cow and having a socket opening opposite said legs and projecting therefrom a plane common with said legs, the improvement comprising:

an elongated shaft having means at one end portion for axial connection with the socket;

windlass means including a reel axially journalled by the other end portion of said shaft;

handle means for rotating said windlass means;

friction grip means including a sleeve-like frame transversely and loosely surrounding said shaft intermediate its ends and being slidable therealong when disposed in a plane normal to the longitudinal axis of said shaft, said sleeve-like frame having an arm projecting laterally of said shaft;

an elongated flexible obstetrical member;

loop means connected with said frame arm for connection with one end portion of said obstetrical member, said windlass means including a windlass line connected with said friction grip means generally opposite its connection with said obstetrical member and said shaft; and, pully means including a pulley mounted on said shaft adjacent said reel for guiding said windlass line toward and away from said reel when the latter is rotated in a windlass line reeling in and paying out direction, respectively, whereby tension simultaneously applied to said obstetrical member and said windlass line permits movement of said friction grip means relative to said shaft and release of tension on either said obstetrical member or said windlass line tilts the plane of said friction grip means toward the axis of said shaft to a friction gripping and binding position thereon.

* * * * *